(12) United States Patent
Raghuwanshi et al.

(10) Patent No.: US 10,519,209 B2
(45) Date of Patent: Dec. 31, 2019

(54) PROCESS FOR PURIFICATION OF RHU-GCSF

(71) Applicant: GENNOVA BIOPHARMACEUTICALS LIMITED, Hinjwadi, Pune (IN)

(72) Inventors: Arjun Raghuwanshi, Pune (IN); Shrawan Kumar Singh, Pune (IN); Nidhiben Thaker, Pune (IN); Shagun Shankar, Pune (IN); Pavan Kardile, Pune (IN); Sanjay Singh, Pune (IN)

(73) Assignee: GENNOVA BIOPHARMACEUTICALS LIMITED, Hinjwadi, Pune (IN)

(*) Notice: Subject to any disclaimer, the term of this patent is extended or adjusted under 35 U.S.C. 154(b) by 0 days.

(21) Appl. No.: 15/326,277

(22) PCT Filed: Jul. 13, 2015

(86) PCT No.: PCT/IN2015/050066
§ 371 (c)(1),
(2) Date: Jan. 13, 2017

(87) PCT Pub. No.: WO2016/009451
PCT Pub. Date: Jan. 21, 2016

(65) Prior Publication Data
US 2017/0210784 A1    Jul. 27, 2017

(30) Foreign Application Priority Data
Jul. 14, 2014 (IN) .......................... 2289/MUM/2014

(51) Int. Cl.
| | | |
|---|---|---|
| C07K 14/535 | (2006.01) |
| A61K 9/00 | (2006.01) |
| A61K 38/19 | (2006.01) |
| A61K 47/02 | (2006.01) |
| A61K 47/10 | (2017.01) |
| A61K 47/12 | (2006.01) |
| A61K 47/26 | (2006.01) |
| C07K 1/02 | (2006.01) |
| C07K 1/14 | (2006.01) |
| C07K 1/18 | (2006.01) |
| C07K 1/34 | (2006.01) |
| A61K 47/60 | (2017.01) |
| A61K 38/00 | (2006.01) |

(52) U.S. Cl.
CPC .......... *C07K 14/535* (2013.01); *A61K 9/0019* (2013.01); *A61K 38/193* (2013.01); *A61K 47/02* (2013.01); *A61K 47/10* (2013.01); *A61K 47/12* (2013.01); *A61K 47/26* (2013.01); *A61K 47/60* (2017.08); *C07K 1/02* (2013.01); *C07K 1/14* (2013.01); *C07K 1/18* (2013.01); *C07K 1/34* (2013.01); *A61K 38/00* (2013.01); *Y02A 50/473* (2018.01)

(58) Field of Classification Search
CPC ................................................... C07K 14/535
See application file for complete search history.

(56) References Cited

FOREIGN PATENT DOCUMENTS

| | | |
|---|---|---|
| EP | 2 341 061 | 7/2011 |
| WO | WO 2008/096370 | 8/2008 |
| WO | WO 2012/021088 | 2/2012 |
| WO | WO 2012/057529 | 5/2012 |

OTHER PUBLICATIONS

Singh and Panda, J. Bioscience and Bioeng. vol. 99: 303-310, 2005.*
International Search Report for PCT/IN2015/050066, dated Feb. 29, 2016, 14 pages.
Vanz et al., "Human granulocyte colony stimulating factor (hG-CSF): cloning, overexpression, purification and characterization", Microbial Call Factories 2008, 7:13, BioMed Central, Apr. 4, 2008, 12 pages.
Herman, et al., Characterization, Formulation, and Stability of Neupogen (Filgrastim), a Recombinant Human Granulocyte-Colony Stimulating Factor, Formulation, Characterization, and Stability of Protein Drugs: Case Histories, vol. 9 of the series Pharmaceutical Biotechnology (2002), pp. 303-328.

* cited by examiner

*Primary Examiner* — Gyan Chandra
(74) *Attorney, Agent, or Firm* — Nixon & Vanderhye P.C.

(57) ABSTRACT

The present invention provides a novel, scalable and industrially viable downstream process for purification of recombinant human G-CSF.

15 Claims, 9 Drawing Sheets

Lane Description:

1: Molecular weight marker
2: Solubilized
3: Refolding
4: Acidified

PROCESS FOR PURIFICATION OF RHU-GCSF

This application is the U.S. national phase of International Application No. PCT/IN2015/050066 filed 13 Jul. 2015, which designated the U.S. and claims priority to IN Patent Application No. 2289/MUM/2014 filed 14 Jul. 2014, the entire contents of each of which are hereby incorporated by reference.

FIELD OF THE INVENTION

The present invention relates to a novel process for purification of proteins. More particularly, the present invention pertains to a process for purification of granulocyte colony stimulating factor (rHu-GCSF).

BACKGROUND OF THE INVENTION

Granulocyte colony-stimulating factor (G-CSF or GCSF) is a glycoprotein that stimulates the bone marrow to produce granulocytes and release them into the bloodstream. In biotherapeutics, G-CSF showed efficacy in treatment of neonatal infections, granulocyte transfusion in patients with neutropenia, in severe infections and sepsis, in acute myeloid leukaemia's made it an essential biopharmaceutical drug. Commercially, two forms of recombinant human G-CSF are available that include *Escherichia coli* (*E. coli*)-derived G-CSF, which has no sugar chain (non-glycosylated G-CSF; filgrastim; Neupogen, Amgen) and Chinese hamster ovary cell derived-CSF (glycosylated G-CSF; lenograstim, Chugai Pharma UK Ltd).

Filgrastim is a water-soluble 175 amino acid protein with a molecular weight of 18,800 Daltons. Filgrastim is obtained from the bacterial fermentation of a strain of *Escherichia coli* (*E. coli*) transformed with a genetically engineered plasmid containing the human G-CSF gene. The biological activities of G-CSF includes stimulation and differentiation of progenitor "stem cells" into a variety of blood cell lines, stimulation of the proliferation of differentiated blood cell lines and stimulating the ultimate differentiation of mature blood cells from proliferated cell lines.

The production of recombinant therapeutic proteins using microorganisms as host system is often difficult because the high-level expression of recombinant proteins leads to the formation of inclusion bodies (IBs) that are insoluble aggregates, as well as the recombinant proteins are present in biologically inactive form which require additional downstream steps to make the protein biologically active and suitable for further purification steps. Moreover, it is often difficult to recover the protein from IBs because of the issues concerned with the initial recovery, solubilization and renaturation steps. The production of recombinant proteins from inclusion bodies can be viable if a simple and cost-effective downstream process may be developed.

The expanding demand for biopharmaceuticals has catalyzed advancement in both upstream as well as downstream processing of biotherapeutic proteins. Significant improvements have been made in the cell culture titers in the last few years and this has moved the centre of bio-pharmaceutical development towards improving the commercial concerns of downstream processing. Protein biotherapeutics are typically produced alongside an assortment of impurities. These include host cell related impurities, process impurities and product related impurities/variants. Of these, the product related impurities/variants are difficult to remove as their physicochemical properties are very similar to the product itself however as these impurities/variants can significantly affect the biological activity of the target therapeutics.

The above mentioned variants/impurities include different oxidation forms of methionine (Met) residues of G-CSF. It is known that, G-CSF protein contains four methionine residues at Met1, Met122, Met127 and Met138 positions. It is observed that at different oxidative conditions, each of the four methionine residues oxidizes at different rates [Met1>Met138>Met127>Met122] which may be resolved by Reverse Phase-High Performance Liquid Chromatography (RP-HPLC) chromatogram to native G-CSF. In addition, impurities like reduced and aggregated form of G-CSF formed by misfolding of native G-CSF demonstrate additional peaks in RP-HPLC chromatogram. These and other such forms of undesired G-CSF leads to reduction in biological activity of native G-CSF. Therefore it is crucial in the pharmaceutical development of therapeutic proteins to remove such impurities during purification process. Furthermore, in RP-HPLC chromatogram, an extra peak of N-formyl methionine variant of G-CSF is also observed along with native G-CSF that possesses the same biological activity as that of native form but sometimes may lead to immunogenic response in patient. The N-formyl methionine variant is a result of partial retention of the formyl group by def gene of *E. coli* due to high level expression of the recombinant proteins. This variant is also an impurity and need to be removed. Thus, its effective removal is a key objective for the purification platforms for bacterial based production of therapeutic proteins.

For removing the aforementioned product related impurities, various chromatographic techniques were used in prior art such as multimodal chromatography which involves the use of resins that offer a combination of interactions between the product and resin like Hydroxy apatite (HA) (cation exchange and metal affinity interaction), Capto MMC (cation exchange and hydrophobic interactions), Capto Adhere (anion exchange and hydrophobic interactions), and HEA/PPA. All of these resins are effective and provide different selectivities but are costly when compared to conventional ion exchange and hydrophobic resins, thereby increasing the cost of the final product. Moreover, optimization of process parameters with multimode resins is a tedious and time consuming process which increases the process development time and subsequently the running time for chromatography.

In last few years development and manufacturing of therapeutic G-CSF involves numerous purification schemes. For instance, WO1987/03689 discloses the use of immune-affinity chromatography for isolation and purification of recombinant G-CSF which was not a well accepted approach for commercial manufacturing, since it could raise its own regulatory concerns. Also the cost of immune-affinity chromatography media was very high compared to conventional chromatography matrices owing to use of monoclonal antibodies for their preparation.

European patent EP2341061, discloses a purification process involving a series of four chromatography steps, comprising two gel filtration chromatographies, a cation exchange chromatography and an anion exchange chromatography for preparation of G-CSF.

Another European patent EP1904522, discloses a purification process used for purification of G-CSF primarily involving three chromatography steps namely, two cation exchange chromatography and a hydrophobic interaction chromatography.

WO 2001/04154 discloses a purification process which includes a hydrophobic interaction chromatography, a hydroxyl apatite chromatography and a cation exchange chromatography to purify the G-CSF. For *E. coli*-derived G-CSF, solubilization of inclusion bodies and refolding of G-CSF are extra steps to be considered. On a commercial scale, due to the multistep process, the final yield decreases to a great extent. Hence a simplified process with fewer steps with higher yields in a shorter time is required.

In prior art, the purification processes described are complicated, long and includes multiple chromatography steps to get the purified G-CSF. Furthermore, none of the earlier processes reveal a basic, prudent and financially practical strategy for the production of G-CSF which could ensure the consistent production of stable product at industrial scale. Subsequently, to conquer the significant issues concerned with the production of G-CSF, a simple, scalable, commercially viable and steadier process for high recovery of G-CSF has been currently developed and disclosed in the present invention. The process of the present invention comprises, streamlined, orthogonal, robust and scalable downstream process steps for production of G-CSF at industrial scale with higher yield and purity.

OBJECT OF THE INVENTION

The object of the present invention is to provide a highly efficient, robust, economical and scalable downstream process for purification of recombinant human G-CSF.

SUMMARY OF THE INVENTION

The present invention provides a novel, scalable and industrially viable downstream process for purification of recombinant human G-CSF.

BRIEF DESCRIPTION OF DRAWING

A list of the accompanying drawing figures is as below.

DETAILED DESCRIPTION OF THE INVENTION

Figure 1:
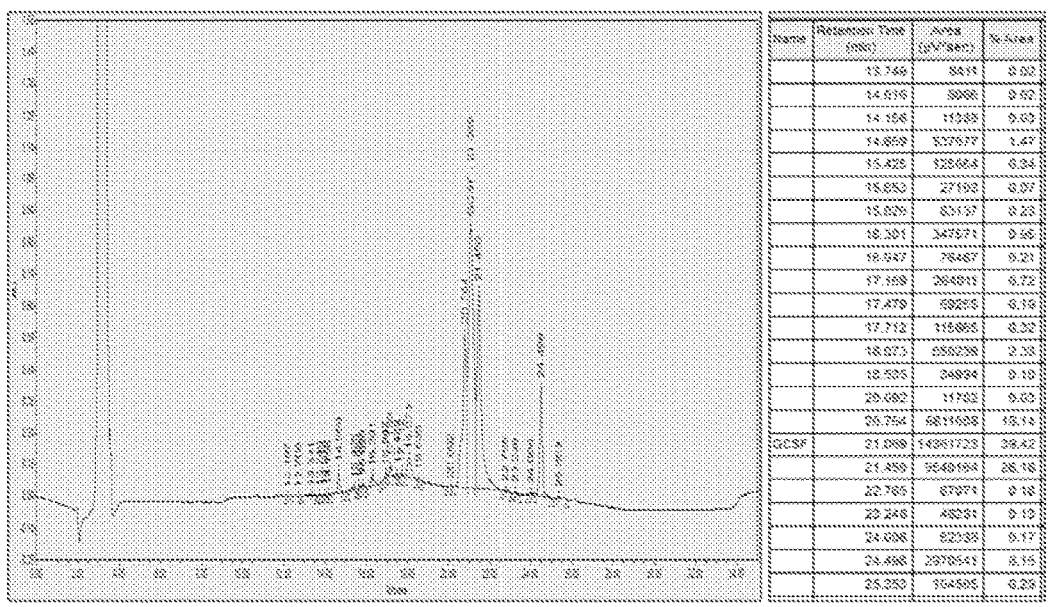
FIG. 1: Depicts the RP-HPLC profile of solubilized IB of rHu-GCSF.

The present invention discloses a process for the isolation and purification of recombinant human granulocyte colony stimulating factor (G-CSF) from a G-CSF producing microorganism. The host cells transformed or transfected with the recombinant plasmids or viral DNA vectors express biologically active human G-CSF or a genetically engineered variant of human G-CSF. The protein expressed is purified using the novel method described in the present invention.

The DNA sequences coding for all or a part of G-CSF includes the incorporation of codons "preferred" for expression by selected non-mammalian hosts. The GCSF gene may be inserted in shuttle plasmid and amplified. The designed vector comprising GCSF open reading frame may then be transformed into a chemically competent host cell and isolated.

The cells may be then grown in fermenter under controlled temperature ranging between 20° C. to 40° C. at pH 5-8, more preferably 25° C. to 30° C. at pH 7.0-7.5. The biomass thus obtained may be subjected to novel isolation and purification process described in the present application to obtain purified GCSF.

A novel process for isolation and purification of G-CSF comprising steps of:
  i. production of rHu-GCSF by high cell density fermentation of *E. coli* and isolation of inclusion bodies;
  ii. solubilization of inclusion bodies obtained from step (i) to release G-CSF;
  iii. refolding of the G-CSF protein obtained from step (ii);
  iv. clarification & purification of G-CSF protein obtained from steps (iii);
  v. optionally conjugating purified G-CSF obtained from step (iv) with PEG;
  vi. optionally purifying the conjugated (pegylated) G-CSF obtained from step (v) using cation exchange chromatography;
  wherein the yield of the process to get purified GCSF from solubilized inclusion bodies ranges from 50 to 70% and purity of G-CSF analyzed by SEC-HPLC is not less than 98%;
  wherein the sum of the impurities such as aggregate is not greater than 2%. Purity of G-CSF as analyzed by RPHPLC is not less than 96.5%;
  wherein the sum of the Oxidized GCSF, Reduced GCSF, f-met GCSF is not greater than 3.5%;
  wherein the yield of process producing PEG-GCSF from GCSF ranges from 60 to 75% and purity of PEG-GCSF as analyzed by SEC-HPLC is not less than 95%.

Production of rHu-GCSF by High Cell Density Fermentation of *E. coli* and Isolation of Inclusion Bodies The purification of GCSF of the present invention may be conducted by production of rHu-GCSF by separating the soluble and particulate fractions of the fermented broth and collecting the biomass. The separation may preferably be carried out by centrifugation, filtration, more preferably by centrifugation.

The separated cells may be further lysed by using lysis buffer at pH 7 to 9, more preferably the pH of the lysis buffer is between pH 7.5-8.5. The cell lysis may be followed by isolation of inclusion bodies.

The isolation may preferably be performed individually or in combination using instruments selected from the group consisting of laboratory scale sonicator, high pressure cell homogenizer, centrifugation, filtration, more preferably a combination of the laboratory scale sonicator and high pressure cell homogenizer.

The isolated inclusion bodies may be further washed with buffers preferably selected from the group consisting of Tris-EDTA-Triton buffer, Tris-EDTA-DOC buffer, Tris-NaCl-Urea buffer, Tris-buffer, TritonX-100; preferably the buffer is mixture of Tris-EDTA, Urea, NaCl and TritonX-100. The concentration of Tris is present in range from 30-50 mM, EDTA is in range from 3-7 mM, Urea is in range from 0.1-0.5 M, NaCl is in range from 1-2 M, and Triton X 100 is in range from 0.8-1.5%. The pH of the washing buffer may be maintained in the range from 7.5-8.5. The temperature of the washing buffer may be maintained in the range from 20 to 25° C. and incubation time is in the range from 60 to 90 minutes.

The selection of the lytic agent and the washing buffer of the present invention are such that it allows higher recovery of inclusion bodies.

Solubilization of Inclusion Bodies Obtained from Step (i) to Release Recombinant Human G-CSF (rHu-G-CSF)

Solubilization of bacterial inclusion bodies is critical step if not optimized properly could affect the yield of further process steps and also the quality of purified protein. The isolated inclusion bodies may be solubilized in a solubilizing mixture of urea, buffer and a reducing agent at an alkaline pH.

The said reducing agent may be preferably selected from the group comprising of 2-mercaptoethanol, dithiothreitol (DTT), cysteine, more preferably the reducing agent is cysteine and present in a range from 20 to 100 mM. The reducing agent may be added at a pH ranging 8-11 for 45 to 120 minutes, more preferably at pH 9-10 for 60 minutes. The selection of the reducing agent of the present invention is such that the solubilization is achieved in 2-3 hrs. The reducing agent may be preferably added after 60 min of solubilization and solubilization is continued for about 60 minutes in the presence of reducing agent. Also the concentration of selected reducing agent is optimized in such a way that it should eliminate the need of adding any reducing agent in refolding buffer. The buffer is selected from the group comprising Tris, EDTA, Urea and their mixture, preferably the buffer is a mixture and the concentration of urea is present in range from 6-8 M, Tris is may be in range from 20-50 mM, EDTA is may be in range from 2-7 mM and the pH of the buffer may be maintained at pH 10 and The pH of solubilizing mixture may be maintained in a range from 9.5-10.5.

The solubilized inclusion bodies solution may be clarified by centrifugation at 8,000-15,000 g for 10-30 minutes, more preferably at 10,000-12,000 g for 30 minutes. The purity of the solubilized IB of rHu-GCSF may be estimated by RP-HPLC profile as represented in FIG. 1. The purity of released G-CSF is found to be in a range from 25-50%.

Refolding of the GCSF Protein Obtained from Step (ii)

A refolding buffer used to refold the proteins is usually composed of chemicals such as guanidium hydrochloride and arginine for increasing the conductivity of refolding solution. Processing of this refolding solution often requires the necessity of having an ultrafiltration/diafiltration step prior to ion exchange chromatography step, which adds extra time, complexity and expenditures to downstream process operations. Keeping these constraints in mind the refolding process of current invention is developed in such a manner that the refolding solution may be directly loaded on to ion exchange chromatography without any extra conditioning step.

Since the protein refolding is generally performed at very low protein concentration, it needs large volume of refolding buffer. Most commonly used component of refolding buffer is arginine which is not only very expensive ingredient to be used in large volume of refolding buffers but also contributes high conductivity to refolding solution which makes it incompatible for loading on to ion exchange chromatography. Hence, the present invention uses a novel and an inventive refolding approach to contribute higher overall yield of downstream process. Also the novel components as claimed in present invention make the process economical and avoid extra unit operations in the process.

For refolding, the clarified solubilized inclusion body solution may be diluted by urea and sorbitol containing refolding buffer optionally comprising of an oxidizing agent.

The said oxidizing agent may preferably be selected from the group consisting of cystine, cysteine, oxidized glutathione (GSSH), cystamine, more preferably oxidizing agent is cystine.

The amount of oxidizing agent may preferably be in the range 0-5 mM, more preferably the amount of cystine is in range of 0-3 mM.

The selection of the oxidizing agent of the present invention is such that higher refolding yield of 85 to 95% and RP-HPLC purity of 40 to 70% may be achieved.

The refolding maybe carried out at room temperature or 2-8° C. for time period of 14-28 hrs, more preferably at room temperature for 12-18 hrs.

The refolded protein solution may optionally be acidified in presence of an acidifying agent. The said acidifying agent may preferably be selected from the group consisting of sodium acetate, acetic acid, hydrochloric acid, orthophosphoric acid, more preferably the acidifying agent is hydrochloric acid.

The pH of the acidified refolded solution may be adjusted in a range from pH 3.0-5.5 and maintained for 20-60 min, more preferably at pH in a range from 3.5 to 4.5 maintained for 30-45 min.

The yield of the refolding step preferably ranges from 50-90%, more preferably the yield is 60-85%.

Figure 2:
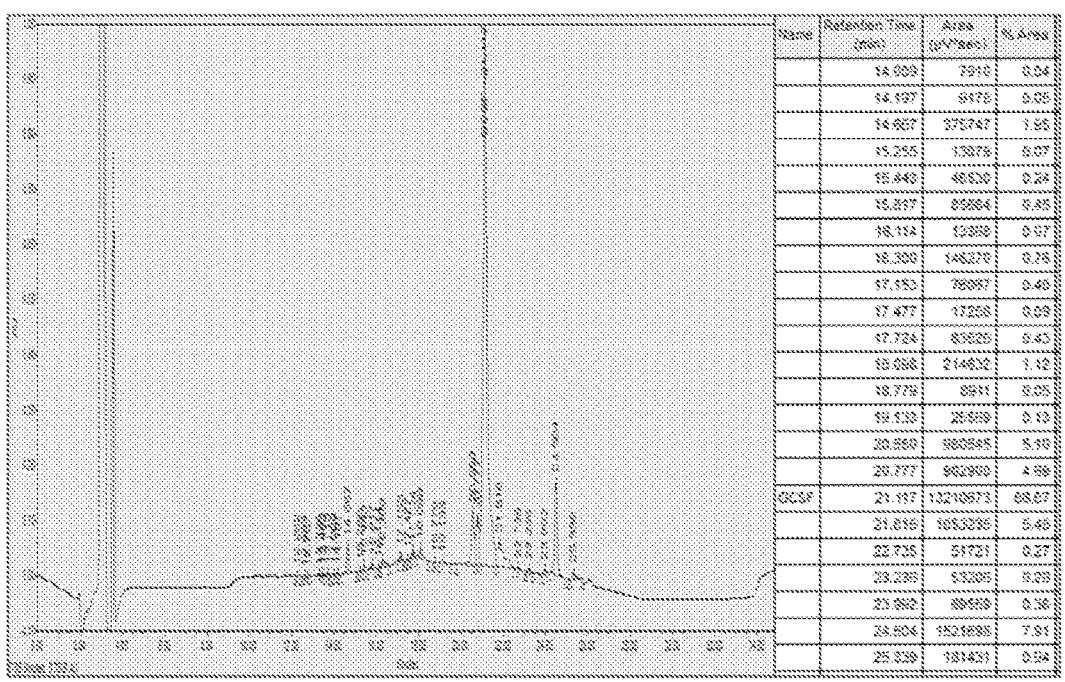
FIG. 2: Depicts the RP-HPLC profile of acidified refolded solution of rHu-GCSF.

The purity of acidified refolded GCSF may be estimated by RP-HPLC profile as represented in FIG. 2.

Figure 3:
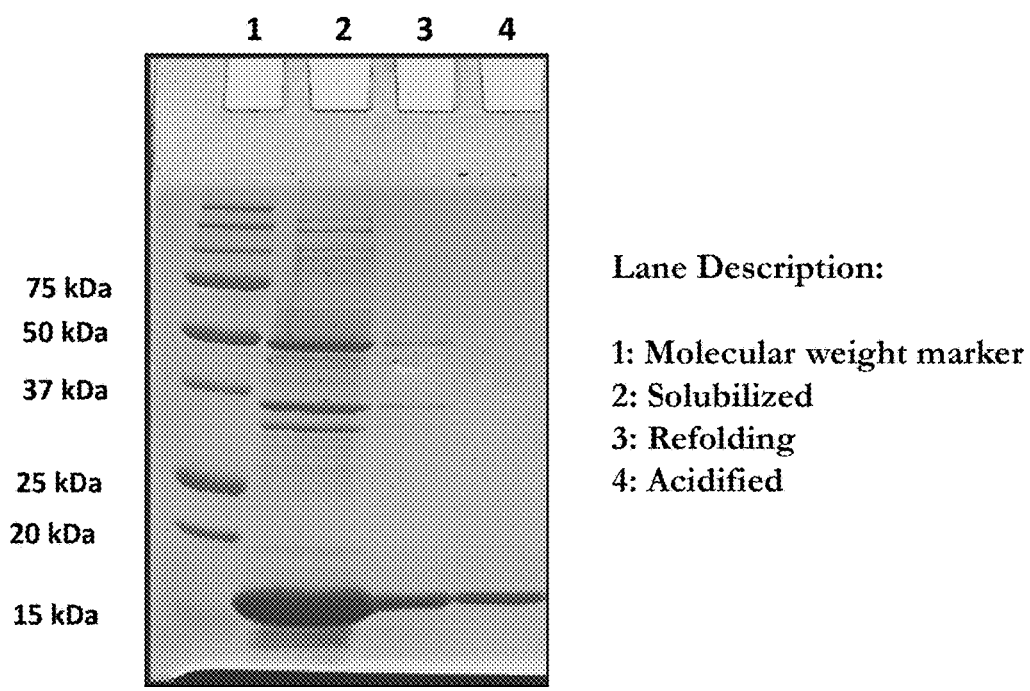
FIG. 3: Depicts the SDS-PAGE profile of solubilized, refolded, and acidified rHu-GCSF samples.

The solubilized solution, refolded solution, acidified solution and ion exchange chromatography eluate may be subjected to SDS-PAGE to characterize low and high molecular weight impurities associated with rHu-GCSF as represented in FIG. 3.

Clarification & Purification of Acidified G-CSF Protein Obtained from Step (iii)

The acidified refolded G-CSF protein solution may optionally be subjected to filtration and/or centrifugation to remove any precipitate and particulate matter that may be formed before subjecting to chromatography for purification.

G-CSF may get precipitated during refolding process and can cause haziness/cloudiness leading to clarification challenges after refolding. Extent of precipitation depends on solubilization followed by refolding strategy. In many such cases, clarification of protein solution involves filtration steps due to broad range of particle size and type present in process stream.

It is preferred to move towards a single step of clarification, particulate removal and/or bio burden reduction to minimize overall production cost. Also it is advantageous to have smaller, more flexible and cost-effective manufacturing facility, which is largely dependent on the selection of unit operations in the process and size of process equipments.

The said clarification may be selected from the group comprising ultrafiltration, diafiltration, microfiltration, depth filtration, tangential flow filtration, normal flow filtration and centrifugation, preferably microfiltration and centrifugation.

The said centrifugation process may be selected from the batch mode and continuous mode, preferably the centrifugation process is continuous process.

Various separation techniques are used to purify proteins depending on its physical and chemical properties.

Methionine oxidized, reduced and f-Met forms of a native recombinant GCSF protein product are certain product variants, which are considered as impurities associated with expression system like *E. coli*. Such product variants differ from native protein in their structural and functional aspects, and may lead to loss of biological activity and immunogenic response in patients. The present invention discloses a two chromatography step purification process for selective removal of these product variants. Unique selectivity in separation of closely related product variants may be obtained using combined pH and salt based elution gradients in ion exchange and hydrophobic interaction chromatography. Complete removal of process related impurities is also achieved in two step purification process.

At present, ion-exchange chromatography (IEC) forms the back-bone of biopharmaceutical drug purification processes due to its high capacity and scalability, however, selective removal of the various product impurities/variants is some-what limited.

In the present invention the proteins may be purified by ion exchange chromatography followed by hydrophobic interaction chromatography wherein process and product related impurities are removed to acceptable limits using combination of pH and salt gradients with high process yields.

The acidified refolded solution may be purified by subjecting it to ion exchange chromatography. The said ion exchange chromatography may either be cation exchange chromatography and anion exchange chromatography, more preferably cation exchange chromatography, most preferably weak cation exchange chromatography. The cation exchange chromatography for purification further comprises a stationary phase and a mobile phase.

The stationary phase of cation exchange chromatography may be selected from the group comprising SP-Sepharose FF, CM-Sepharose FF, SP-Sepharose HP, Fractogel S03, Fractogel SE Hi Cap, more preferably CM-Sepharose FF.

The mobile phase or binding buffer of cation exchange chromatography is selected from the group comprising sodium acetate, acetic acid, sodium phosphate, orthophosphoric acid or a mixture, preferably a mixture comprises sodium acetate and acetic acid. The concentration of mobile phase or binding buffer is 20-50 mM, and pH ranges from 3.5-4.5.

The GCSF protein is eluted out of cation exchange column using the buffer comprises a mixture of sodium acetate, acetic acid and NaCl, at a pH range from 4.0-6.0 preferably in the range from 4.5-5.6. The mode of elution is selected from the group comprising step gradient, linear gradient and/or combination of both, preferably the gradient used for elution is step gradient.

Refolded and acidified solutions containing G-CSF may be applied to cation exchange media under acidic conditions, for example at pH 3.0 to pH 5.0, and eluted from the media at weakly acidic to weakly basic pH, for example from pH 4.0 to pH 8. G-CSF may be eluted from the cation exchange medium at slightly acidic conditions, using an increasing gradient of NaCl or other salt, e.g., 0-200mM-NaCl, in 40-50 mM sodium acetate, pH 5.4. Alternatively, rHu-G-CSF may be eluted from the cation exchange medium at slightly basic conditions, using 40-50 mM sodium acetate at pH 5.6-6.2 with or without using any salt.

The elution may be preferably performed at a flow rate of 100-250 cm/hr, more preferably 150-200 cm/hr. The dynamic binding capacity may be preferably between 10-20 mg/ml, more preferably 15-18 mg/ml.

The yield of ion exchange chromatography step may preferably be in the range of 70-98%, more preferably 90-98%.

Figure 4:
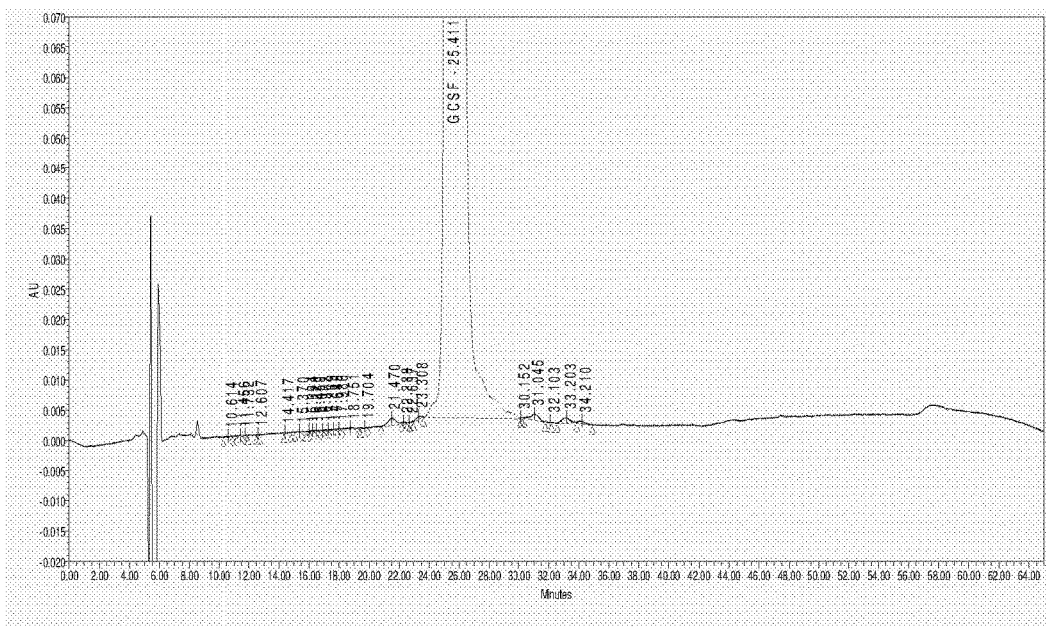
FIG. 4: Depicts the RP-HPLC profile of Ion Exchange Chromatography-I Elute.

The selection of the cation exchange media of the present invention may be such that the medium is conditioned using a small volume of refolded solution and which avoids use of extra unit operation like buffer exchange chromatography or diafiltration using TFF. The purity of ion exchange eluate may be estimated by RP-HPLC profile as represented in FIG. 4. The RP-HPLC purity of G-CSF obtained from cation exchange chromatography step is in a range of 90%-97%.

The ion exchange chromatography eluate containing rHu-G-CSF may be applied to hydrophobic interaction media under acidic conditions preferably in the range of pH 2.0 to pH 7.0, more preferably pH 4.0 to pH 6.0.

The ion exchange chromatography eluate is diluted with ammonium sulphate to ensure the effective concentration of ammonium sulphate in diluted solution remains in the range from 0.5-1.5 M, preferably in the range from 0.7-1.0 M.

The hydrophobic interaction media or stationary phase of the present invention may be selected from the group comprising Phenyl Sepharose FF, Butyl Sepharose, Nuviac-Prime, HEA hypercel, PPA hypercel, Phenyl Sepharose HP, MEP hyper cell, and Capto Adhere, preferably phenyl Sepharose FF.

The mobile phase or binding buffer of hydrophobic interaction chromatography comprises mixture of sodium acetate, acetic acid, and ammonium sulfate at a pH range from 4.5-6, more preferably the pH is in the range of 5.2-5.8.

The elution may be preferably performed at a flow rate of 95-300 cm/hr, more preferably at 100-250 cm/hr.

The purified GCSF protein is eluted from the stationary phase of hydrophobic interaction chromatography using mobile phase comprises sodium acetate and acetic acid at a pH range from 4-6, more preferably in the range of 4.0-5.0. The mode of elution is selected from the group comprising step gradient, linear gradient and combination of both, preferably the gradient used for elution is step gradient.

The eluate is obtained at a flow rate from 95-300 cm/hr, preferably 100-250 cm/hr. The yield of the hydrophobic interaction chromatography (HIC) step may preferably ranges between 80 to 90%.The purity of G-CSF protein obtained from hydrophobic interaction chromatography is in a range from 96.5%-99.5%.

Figure 5:
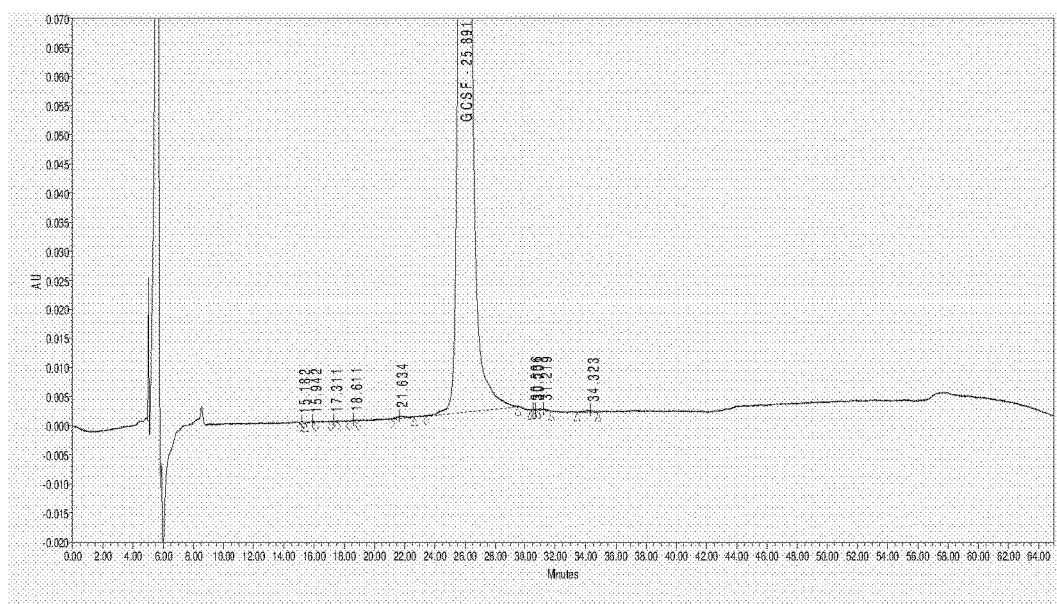
FIG. 5: Depicts the RP-HPLC profile of Hydrophobic Interaction eluate.

The selection of second chromatography of the present invention may be such that final purity of GCSF achieved to match the quality required for pharmaceutical preparation of rHu-GCSF. The purity of HIC eluate may be estimated by RP-HPLC profile as represented in FIG. 5.

The HIC load, wash-I may be subjected to SDS-PAGE to characterize low and high molecular weight impurities associated with rHu-GCSF.

Results indicate that the product recovery after two chromatography step purification is up to 50 to 70.0% with purity levels of greater than 98.0%. Selective removal of various product variants using the combined pH and salt based elution and removal of the host cell impurities using orthogonal selection of chromatography steps are amongst the novel and inventive features of the process of the present invention.

Figure 6:
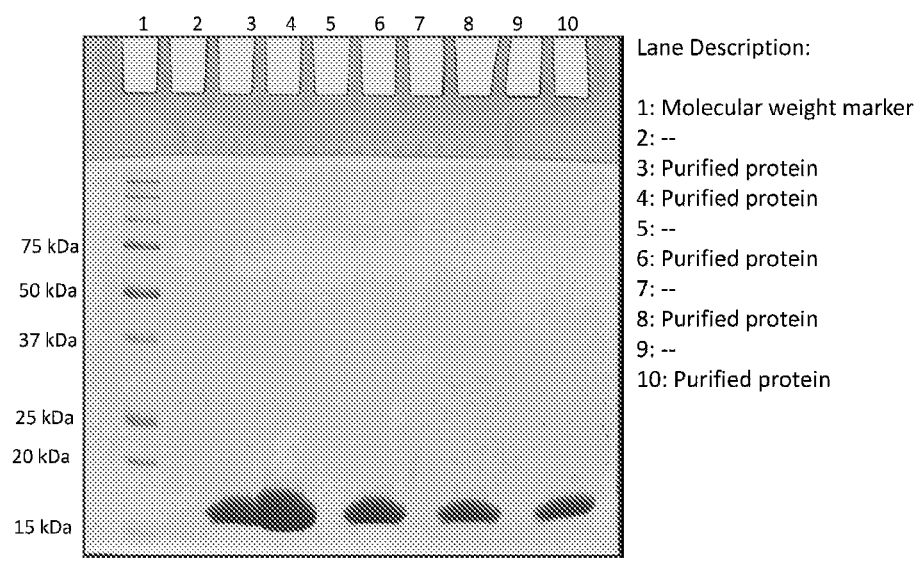
FIG. 6: Depicts the SDS-PAGE profile of purified rHu-GCSF protein.
Figure 7:
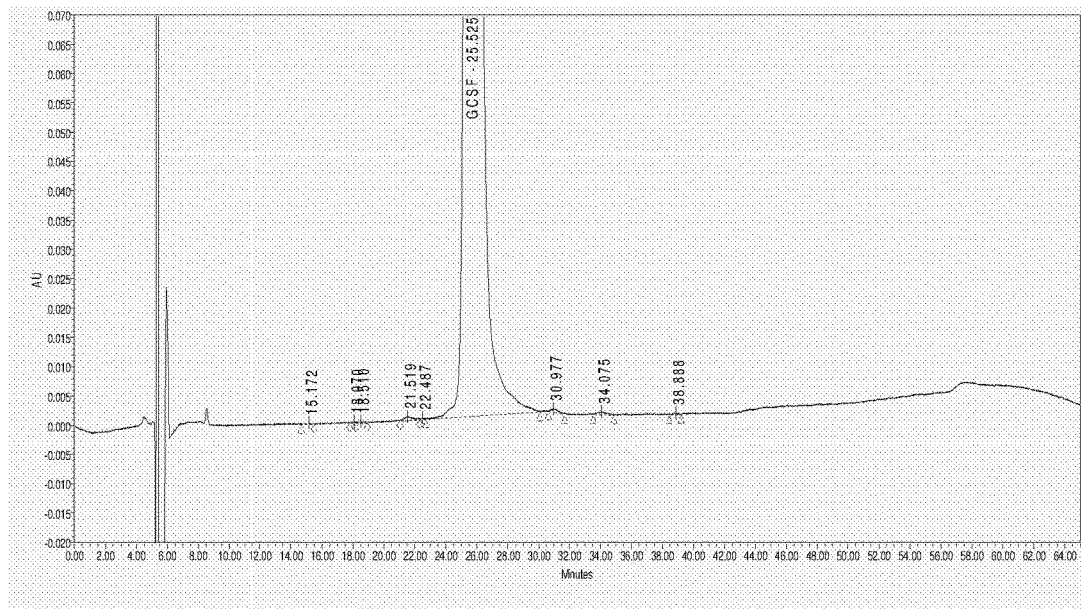
FIG. 7: Depicts the RP-HPLC profile of purified rHu-GCSF protein.

The eluate of hydrophobic interaction chromatography may optionally be buffer exchanged in formulation buffer. The refolded G-CSF in formulation buffer containing biologically active G-CSF may be sterile filtered to produce the pharmaceutical grade recombinant human G-CSF having final concentration in range of 0.5 to 0.9 mg/ml, more preferably 0.85 to 0.90 mg/ml. The purity of final purified protein may be estimated by RP-HPLC profile as represented in FIG. 6.

The recombinant human G-CSF obtained by the process described in the present invention can be useful in the treatment of medical conditions related to haematology and oncology. E.g. neutropenia, acute myeloid leukaemia and a variety of infections in humans, animals, poultry, swine, horses, as well as dogs and cats are treatable with administration of G-CSF of current invention.

Optionally Conjugating Purified G-CSF Obtained from Step (iv) with PEG

Purified rHu-GCSF (Drug Substance) may be conjugated with a polyethylene glycol in a suitable buffer at an acidic pH.

The said buffer may be preferably selected from group comprising sodium acetate, phosphate acetate, potassium hydrogen phosphate, potassium dihydrogen phosphate, disodium hydrogen phosphate, potassium hydrogen phthalate, sodium tetraborate, more preferably sodium acetate.

pH of the said conjugation reaction may be preferably in range of pH 5.0 to 5.8. The said conjugation reaction may be carried out by adding 3 to 5 times higher quantity (w/w) of 20kD PEG aldehyde compared to purified rHu-GCSF used for conjugation reaction.

The said conjugation reaction may optionally be carried in presence of a reducing agent preferably selected from the group comprising sodium cyanoborohydride, sodium triacetoxy borohydride, sodium borohydride, sodium dithionite, sodium hydrosulfite, more preferably sodium cyanoborohydride.

The reducing agent may preferably be added at a concentration in the range of 10 to 30 mM, more preferably 20 mM. The reaction mixture may be stirred at room temperature for 12 to 18 hrs, more preferably for 12-16 hrs. The yield of monopegylated rHu-GCSF preferably is in the range of 65 to 85%, more preferably 70 to 75%. The monopegylated rHu-GCSF reaction mixture may be preferably stored at 1 to 10° C. for further purification, more preferably at 2-8° C.

Optionally Purification of Conjugated (Pegylated) G-CSF Obtained from Step (v) by Using Cation Exchange Chromatography The conjugated pegylated G-CSF mixture may be diluted with equilibration buffer and pH is adjusted in range of 3.5-5.0, more preferably pH may be adjusted to 4.0-4.5.

The said diluted sample may be subjected to ion exchange chromatography, more preferably cation exchange chromatography. The cation exchange chromatography comprises stationary phase or cation exchange media and mobile phase or binding buffer the stationary phase or cation exchange media is selected from the group comprising of MacroCap-SP and SP Sepharose FF, Fractogel S03, preferably the stationary phase is MacroCap-SP. The elution buffer or elution mobile phase is selected from the sodium acetate, acetic acid, Sodium Chloride and their mixture, preferably mobile phase is a mixture. The concentration of sodium acetate is in the range of 10-50 mM and Sodium Chloride in the range of 0.25 to 0.75 M. The pH of the elution buffer or elution mobile phase is present in the range from 3.5-5, preferably the pH is 4.0-4.5. The mode of elution is selected from the group comprising step gradient, linear gradient and combination of both; preferably the gradient used for elution is step gradient. The yield of monopegylated GCSF obtained from cation exchange chromatography is in the range from 80 to 95% preferably the range is from 85 to 90%.

Figure 8:
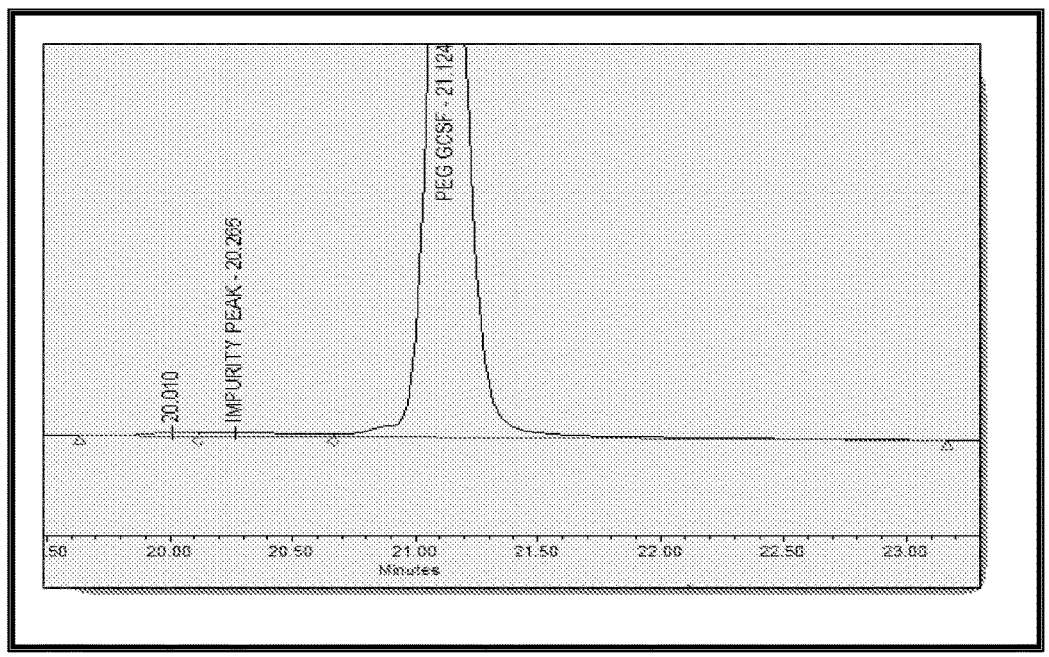
FIG. 8: Depicts the RP-HPLC profile of purified PEG-GCSF protein.
Figure 9:
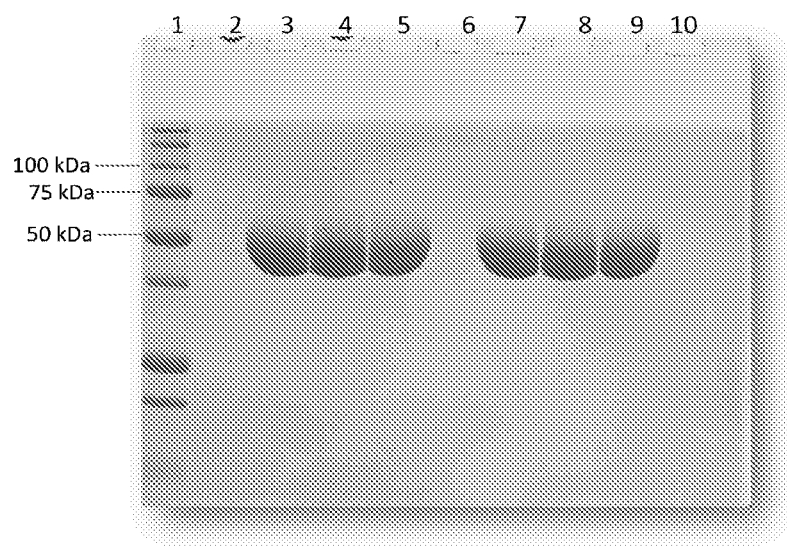
FIG. 9: Depicts the SDS-PAGE profile of purified PEG-GCSF protein.

Purified monopegylated r-Hu-GCSF may be recovered and eluted from the column by performing elution at a flow rate of 100-150 cm/hr, more preferably 100 cm/hr. All the chromatography samples including load, flow through, washes, and elution may be analyzed using following analytical methods:

a) RP-HPLC for identification and purity analysis as represented in FIG. 8;
b) SDS PAGE (reduced) for purity analysis as represented in FIG. 9;
c) Total Protein by Bradford.

Target Elute fraction may be buffer exchanged in predefined formulation buffer of pegfilgrastim containing sodium acetate and sorbitol at pH preferably ranging between pH 3.0-4.0, more preferably pH 4.0-4.5.

The purified monopegylated rHu-GCSF may be further concentrated up to 9-12 mg/ml by 10 kDa ultra filtration membrane, more preferably the purified monopegylated rHu-GCSF may be concentrated in range of 11.0-11.5 mg/ml.

The final TFF retentate thus obtained may be sterile filtered with 0.2 micron to get filtrate of intended quality and diluted by formulation buffer during sterile filtration to recover the product holdup, filtration may be optimized to recover the product at pegfilgrastim concentration of >10 mg/ml.

The final purified monopegylated rHu-GCSF produced may be preferably stored at temperature ranging from 1-10° C., more preferably at 2-8° C. till further use.

The final PEG-GCSF concentrated solution may analyzed by following analytical methods to check the PEG-GCSF concentrated solution or PEG-GCSF drug substance or PEG-GCSF bulk drug substance or PEG-GCSF API against specification.

a) Appearance and pH;
b) Identity and purity check by SDS PAGE, Western Blot, N-terminal sequence analysis, Isoelectric focusing (IEF) and peptide map;
c) HCP determination using ELISA;
d) Bioactivity as per specification;
e) Host cell DNA quantification using q PCR;
f) Endotoxin quantification using LAL test;
g) Aggregate by size exclusion HPLC;
h) Related impurities by RP-HPLC; and
i) Sterility as per specification.

After extensive analysis and biophysical comparison with innovator product it may be concluded that the product purified by the process described in the present invention is N-terminal monopegylated GCSF which is highly similar to innovator product with overall process yield of more than 65%.

The rHu-GCSF and rHu PEG-GCSF drug substances obtained using process described in present invention are extensively characterized using monograph and state of art in house analytical methods. The rHu-GCSF product obtained using process of present invention meets following critical quality attributes but not limited to the critical quality attribute results set out in detail at Table 1 & Table 2:

TABLE 1

Quality of rHu-GCSF obtained using process of the present invention

| Critical Quality Attribute (CQA) | Results obtained for rHu-GCSF |
|---|---|
| Appearance | Clear, colourless to slightly yellowish liquid |

TABLE 1-continued

Quality of rHu-GCSF obtained using process of the present invention

| Critical Quality Attribute (CQA) | Results obtained for rHu-GCSF |
|---|---|
| Identification A - by Assay | Should show biological activity as described under pharmacopoeia assay |
| Identification B - determination by Isoelectric focusing (impurities with charge different from that of Filgrastim) | The principle band in the electropherogram obtained with the test solution is similar in the position to the principle band obtained with the reference solution. |
| Identification C - determination by size exclusion chromatography (impurities of molecular mass higher than that of Filgrastim/ dimers and related substance of higher molecular mass) | The retention time to the principle peak obtained with test solution is similar to that of the principal peak obtained with the reference solution. |
| Identification D - determination by polyacrylamide gel electrophoresis under reducing and non-reducing condition size exclusion chromatography (impurities of molecular mass differing that of Filgrastim) | The electropherogram obtained under both reducing and non-reducing condition, the principle band obtained with the test solution is similar in the position to the principle band obtained with the reference solution. |
| Activity (Potency) | 80-125% of the stated potency (should not be less than $1 \times 10^8$ IU of Filgrastim/mg of protein) |
| RP-HPLC Purity | Not Less Than 96.5% to 99.8% |
| Related proteins (total impurities) by reverse phase HPLC | Area of any peak other than principle peak is not more than 2% of total area of all peaks. The sum of the area of all the peaks other than principle peaks is not more than 3.5% of the total area of peaks. |
| Oxidized GCSF | Below 1.5% |
| Reduced GCSF | Below 1% |
| f-met GCSF | Below 1.5% |
| Dimer and related substance of higher molecular mass determined by size exclusion chromatography | Total of the peaks with retention time less than principle peak should be less than 2%. |
| HCP | Below 100 ppm |
| DNA | Below 10 ng/dose |
| Endotoxin | Below 2 EU/mg |
| Protein Content | Not less than 0.9 mg/ml |
| Sterility | Should complies as per pharmacopoeia test of sterility |

TABLE 2

Quality of rHu PEG- GCSF (PEG-FILGRASTIM) obtained using method of the present invention

| Critical Quality Attributes (CQAs) | Results obtained for PEG GCSF |
|---|---|
| Appearance | Clear, colourless or slightly yellowish liquid |
| Identification A by Potency | Complies with the requirements described under pharmacopoeia potency assay |
| Identification B by impurities with molecular masses higher than that of Pegfilgrastim | The principle peak in the chromatogram obtained with test solution is similar retention time to the principal peak in the chromatogram obtained with the reference solution. |
| Identification C by impurities with molecular masses differing from that of pegfilgrastim | The principle band in the electropherogram obtained with the test solution is similar in the position to the principle band obtained with the reference solution. |
| pH | Between 3.7 and 4.3 |
| Protein Content | Not less than 10 mg/ml |
| Impurities with molecular masses higher than Peg-Filgrastim | Total of the peaks with retention time less than principle peak should be less than 5%. |
| Potency | Between 80% to 120% |

TABLE 2-continued

Quality of rHu PEG- GCSF (PEG-FILGRASTIM) obtained using method of the present invention

| Critical Quality Attributes (CQAs) | Results obtained for PEG GCSF |
|---|---|
| Free mPEG Aldehyde | NMT 0.016 mg/ml |
| Sterility | Should complies as per pharmacopoeia test of sterility |

From Table 1 & Table 2 it may be seen that the rHu-GCSF & rHu PEG-GCSF obtained by the process of the present invention has a greater potency with much less impurity profile.

In the present invention, the above mentioned improvements in the purification process of yielding rHu-GCSF (filgrastim) and PEG-GCSF (Pegfilgrastim) would be beneficial in terms of decreased human intervention, capital expenditure and operational expenditure costs in addition to an expected higher overall product yield.

In an embodiment the present invention also discloses pharmaceutical compositions of G-CSF in a pharmaceutically acceptable carrier. These compositions may be administered intravascularly, intraperitoneally, subcutaneously, intramuscularly, or by using forms known to the pharmaceutical art. For intravascular, intraperitoneal, subcutaneous, intramuscular, active drug components may be combined with a suitable carrier such as water, saline, aqueous dextrose, and the like.

In an embodiment the present invention provides a pharmaceutical composition comprising the G-CSF obtained from the process of present invention in liquid parenteral I.V formulation with pharmaceutically acceptable excipients for proliferation and differentiation of granulocytes.

In an embodiment the pharmaceutical composition of present invention comprises: G-CSF or Filgrastim obtained from the process of present invention formulated in a 10 mM sodium acetate buffer at pH 4.0, containing 5% sorbitol and 0.004% Polysorbate 80.

| Ingredient | Quantity |
|---|---|
| Filgrastim | More than 0.9 mg |
| Acetate | 0.59 mg |
| Sorbitol | 50.0 mg |
| Polysorbate 80 | 0.04 mg |
| Sodium | 0.035 mg |
| Water for Injection | Q.S. to 1 ml |

In an embodiment the pharmaceutical composition of present invention comprises: PEG-GCSF/Peg-Filgrastim obtained from the process of present invention formulated in a 10 mM sodium acetate buffer at pH 4.0, containing 5% sorbitol and 0.004% Polysorbate 20.

| Ingredient | Quantity |
|---|---|
| Peg- Filgrastim | More than 10 mg |
| Acetate | 0.59 mg |
| Sorbitol | 50.0 mg |
| Polysorbate 20 | 0.04 mg |
| Sodium | 0.035 mg |
| Water for Injection | Q.S. to 1 ml |

In another embodiment the present invention provides use of the isolated and prepared GCSF as claimed in claim 1, in liquid parenteral, I.V formulation for proliferation and differentiation of granulocytes.

The invention according to present invention may be illustrated by the following examples which are not to be construed as limiting the scope of the invention:

EXAMPLE-1: PROCESS OF ISOLATION AND PURIFICATION OF G-CSF OF PRESENT INVENTION

Step 1: Production of rHu-GCSF by high cell density fermentation of E. coli The pre-inoculum medium containing suitable antibiotic is inoculated with E. coli cells from Petri plate revived from frozen stock. Culture is incubated at 30° C., 12 Hrs. at 250 rpm. The pre inoculum and subsequently inoculum are prepared by inoculating E. coli in basal media containing suitable antibiotics and incubated at 30° C., 12 Hrs. at 250 rpm. Fermenter containing conditioned basal salt medium is inoculated with inoculum culture such that the starting O.D. at 600 nm is approx. 0.1. Culture is induced by adding 1 mM IPTG when desired O.D.600 nm is reached. During induced fed-batch cultivation, following induction, broth containing induced E. coli cells is harvested by centrifugation at 4° C. and 6000 rpm for 30 min. The harvested cell pellet is washed with phosphate buffered saline (PBS). The washed pelleted cells are stored at −80° C. till further processing.

Step 2: Cell Lysis, Isolation and Washing of Inclusion Bodies 19.0 g of frozen cell pellet obtained from fermentation and diluted 15× in Lysis Buffer comprises 100 mM Tris, 20 mM EDTA, 250 mM NaCl, and pH 8.0. Solution kept for stirring at room temperature (RT) for 30 min.

After 30 min of stirring cell suspension is homogenized at high pressure using high pressure homogenizer (PANDA, Niro Soavi) at 1000 bar. Complete cell suspension is homogenized for three passes. Cell lysis is monitored by checking drop in OD 600 nm and observing under light microscopy.

After three passes of lysis, cell lysate is subjected to high speed centrifugation at 10,000 g for 20 min. Lysed cell pellet is carefully recovered by decanting the supernatant. Both lysed pellet and supernatant were analyzed by reducing SDS PAGE.

Lysed cell pellet obtained after centrifugation is again resuspended in wash buffer containing 20 mM Tris, 1% Triton X 100, 5 mM EDTA, and pH 8.0. Suspension is kept for stirring at room temperature for 30 min. After 30 minutes of incubation and stirring in wash buffer the suspension is subjected to centrifugation at 10,000 g for 20 min. Washed IB is recovered in pellet fraction by carefully decanting the supernatant. Both washed IB and supernatant were analyzed by reducing SDS PAGE for purity estimation. Washed Inclusion bodies (TB) were stored at −80° C. till further use.

Step 3: Solubilization of Inclusion Bodies to Release GCSF 1 g of Inclusion body weighed and solubilized in 20 ml of solubilization buffer comprises; 50 mM Tris, 5 mM EDTA and 8M Urea at pH 10. After 1 hr of solubilization, 40 mM Cysteine was added to reduce the disulfide bonds, pH was readjusted to 10.0 and kept for solubilization for 60 minutes at room temperature with continuous stirring. After solubilization, the solubilized inclusion body solution was clarified using centrifugation at 11000 g for 30 minutes.

Step 4: Refolding of the GCSF Protein

The clarified and solubilized inclusion body solution was refolded by adding it slowly into 10 volumes of refolding buffer composed of 50 mM Tris, 0.5M Urea, 5% Sorbitol and 2 mM Cystine. Dilution is carried out using pump with constant flow rate. After addition of solubilized sample to refolding buffer sample was kept overnight (approximately 16 hr) for refolding at room temperature (25° C.).

a) SDS PAGE (reduced) for purity analysis;
b) RP-HPLC for identification and purity analysis;
c) Total Protein by Bradford.

Step 5: Clarification of Acidified G-CSF Protein Refolded Solution

Refolded clarified protein solution was acidified by addition of stock solution of 1 M sodium acetate pH 4.0 equivalent to 20 mM Sodium Acetate and finally pH was adjusted by 2M hydrochloric acid up to pH 4.0 and kept for 30 min on hold.

The acidified refolded G-CSF protein solution may optionally be subjected to filtration to remove any precipitate and particulate matter that may be formed before subjecting to chromatography. The said filtration may be preferably selected from the group comprising ultrafiltration, diafiltration, microfiltration, depth filtration, tangential flow filtration, normal flow filtration and centrifugation, preferably microfiltration.

If clarification by filtration is selected, the selection is based on performance to effectively remove colloids, aggregates, precipitates and particles up to an extent that it can be directly loaded and protects downstream chromatography column. Final selection is made on the basis of overall optimum filtrate quality and cost of filtration. General selection criteria of filters are as below but not limited to:

a) Flux
b) Throughput
c) Reusability
d) Sterilization Cycles
e) Non-Fiber releasing
f) Filtrate quality
g) Cost of Filtration/L/RUN
h) Equipment footprint Step 6: Purification by Chromatography After acidification solution was filtered by 0.2μ filter microfiltration to remove precipitates and loaded on to 2 ml of pre-equilibrated cation exchange column. Column was washed for 5 CV with equilibration buffer composed of 40 mM Sodium acetate, pH 4.0 to bring the UV280 absorbance to baseline. Column was further washed to remove product related impurities with wash buffer containing 40 mM Sodium acetate pH 5.5. After washing the purified rHu-GCSF was recovered and eluted from the column by passing elution buffer composed of 40 mM sodium acetate, 200 mM sodium chloride at pH 5.4 All the chromatography samples including load, flow through, washes, and elution are analyzed using following analytical methods: Cation exchange chromatography elution fractions containing purified rHu GCSF were pooled and diluted 1:1 with buffer composed of 20 mM sodium acetate, 1.5 M ammonium sulphate, pH 5.4. Diluted solution was filtered by 0.2μ filter to remove precipitates and to remove and loaded on to 1 ml of pre equilibrated HIC column. Column was washed for 5 CV with equilibration buffer composed of 20 mM Sodium Acetate buffer, and 0.8M Ammonium Sulphate, pH 5.4 to bring the UV280 absorbance to baseline. Target protein was recovered and eluted from the column running a linear gradient of equilibration and elution buffer comprises of 20 mM sodium acetate buffer, pH4.0 in 20CV.

All the chromatography samples including load, flow through, washes, and elution are analyzed using following analytical methods:

a) SDS PAGE (reduced) for purity analysis;
b) RP-HPLC for identification and purity analysis;
c) Total Protein by Bradford;

d) HCP determination using ELISA;

e) Endotoxin quantification using LAL test.

Step 7: Recovering the Purified G-CSF in Formulation Buffer

HIC fractions containing purified target protein was buffer exchanged in predefined formulation buffer composed of 10 mM sodium, pH 4.0, 5% Sorbitol, 0.004% Polysorbate 80 and further concentrated up to 1 mg/ml using 10 kDa of ultra filtration membrane. The final rHu-GCSF concentrated solution was sterile filtered with 0.2 micron and stored at 2-8° C. till further use.

The final G-CSF concentrated solution was analyzed by following analytical methods to check the G-CSF concentrated solution or G-CSF drug substance or G-CSF bulk drug substance or G-CSF API against specification.

a) Appearance and pH;

b) Identity and purity check by SDS PAGE, Western Blot, N-terminal sequence analysis, Isoelectric focusing (IEF) and peptide map;

c) HCP determination using ELISA;

d) Bioactivity as per specification;

e) Host cell DNA quantification using q PCR;

f) Endotoxin quantification using LAL test;

g) Aggregate by size exclusion HPLC;

h) Related impurities by RP-HPLC;

i) Sterility as per specification.

Step 8: Conjugation and Purification of Pegylated G-CSF Using Cation Exchange Chromatography Purified rHu-GCSF present in 10 mM sodium acetate buffer, pH 4.0, containing 5% sorbitol and 0.004% Tween 80 at a concentration of 1-1.2 mg/mL is adjusted to pH ~5.0 by addition of 1 M Sodium acetate at pH 5.0. The final buffer strength is approximately 50 mM. The 3× amount (weight basis) of mPEG-20 kDa-CHO is added to the reaction mixture mPEG-20 kDa-PEG-aldehyde to the amount of rHu-GCSF present in reaction mixture before pegylation. Immediately 20 mM Sodium Cyanoborohydride [Na(CN)BH$_3$] is added to the reaction mixture. The reaction mixture is stirred at room temperature [~25° C.] overnight. In process quality analysis is performed to check the % of monopegylated filgrastim, generally 75-80% monopegylated filgrastim is obtained after 14 hrs, reaction is quenched with 1M tris at pH 8.0 and stored at 2-8° C. till further processing.

Conjugation reaction mixture is 20× diluted with Equilibration buffer and pH is adjusted to 4.0. Diluted sample is loaded onto pre-equilibrated cation exchange chromatography column (MacroCap SP) at a liner flow rate of 100 cm/hr. Column is washed for 5 CV with equilibration buffer composed of 20 mM Sodium Acetate, pH 4.0 to bring the UV280 absorbance to baseline at a liner flow rate of 100 cm/hr. Purified N-terminally Monopegylated rHu-GCSF is recovered and eluted from the column by passing elution buffer composed of 20 mM Sodium Acetate, 0.5 M NaCl, pH 4.0 in 0-100% liner gradient for 10 CV at a liner flow rate of 100 cm/hr.

All the chromatography samples including load, flow through, washes, and elution are analyzed using following analytical methods:

d) SDS PAGE (reduced) for purity analysis;

e) RP-HPLC for identification and purity analysis;

f) Total Protein by Bradford.

Target fraction of chromatography eluate is buffer exchanged in buffer containing 10 mM Sodium Acetate, 5% Sorbitol, 0.004% Polysorbate 20, pH 4.0.

Buffer exchanged sample is further concentrated up to ~11 mg/ml by 10 kDa ultra filtration membrane. The final TFF retentate is sterile filtered with 0.2 micron to get filtrate of intended quality and diluted using buffer. During sterile filtration to recover the product holdup, filtration is optimized to recover the product at PEG-GCSF concentration of >10 mg/ml. The final product is stored at 2-8° C. till further use.

The final pegfilgrastim concentrated solution is analyzed by following analytical methods to check the pegfilgrastim concentrated solution or pegfilgrastim drug substance or pegfilgrastim bulk drug substance or pegfilgrastim API against specification.

j) Appearance and pH;

k) Identity and purity check by SDS PAGE, Western Blot, N-terminal sequence analysis, Isoelectric focusing (IEF) and peptide map;

l) HCP determination using ELISA;

m) Bioactivity as per specification;

n) Host cell DNA quantification using q PCR;

o) Endotoxin quantification using LAL test;

p) Aggregate by size exclusion HPLC;

q) Related impurities by RP-HPLC; and r) Sterility as per specification.

In the present invention, the aforementioned improvements in the purification process of PEG-GCSF will be beneficial in terms of decreased human intervention, capital expenditure and operational expenditure costs in addition to an expected higher overall product yield in the final product.

The invention claimed is:

1. A scalable industrial process for isolation and purification of granulocyte colony stimulating factor (G-CSF) comprising:

i. isolating inclusion bodies comprising G-CSF from *E. coli* cells produced by high cell density fermentation, comprising lysing the *E. coli* cells in a lysis buffer comprising Tris, EDTA and NaCl, wherein the isolating inclusion bodies is performed by instruments selected from the group consisting of laboratory scale sonicator, high pressure cell homogenizer, centrifuge and filtration device;

ii. solubilizing the G-CSF by incubating the isolated inclusion bodies obtained from step (i) in a solubilization reaction, which comprises Tris, EDTA and Urea, wherein a reducing agent comprising cysteine is added to the solubilization reaction after 1 hour of incubation;

iii. refolding the solubilized G-CSF obtained from step (ii) by diluting the solubilized G-CSF into a refolding buffer to create a refolding reaction and incubating the refolding reaction for 12 to 28 hours at room temperature, wherein the refolding buffer comprises Tris, urea, sorbitol and an oxidizing agent selected from the group cystine, oxidized glutathione (GSSH) and cystamine;

iv. acidifying the refolded G-CSF solution obtained from step (iii) by adding to the refolding reaction sodium acetate and an acidifying agent selected from the group of acetic acid, hydrochloric acid and orthophosphoric acid in an amount sufficient to arrive at a pH in the range of 3.0 to 5.5;

v. clarifying the acidified G-CSF solution obtained from step (iv); wherein the clarification is performed by one or both of filtration and centrifugation, and vi. purifying G-CSF from the clarified G-CSF solution obtained from step (v) by cation exchange chromatography followed by hydrophobic interaction chromatography (HIC);

wherein each of the cation exchange chromatography and the hydrophobic interaction chromatography comprise a stationary phase and a mobile phase, wherein the G-CSF is recombinant human granulocyte colony stimulating factor, and wherein the yield of the process ranges from 50% to 70%.

2. The process of claim 1, further comprising:
vii. conjugating the purified G-CSF obtained from step (vi) with PEG to produce monopegylated G-CSF by incubating a stirred conjugation reaction mixture comprising a conjugation buffer solution, a PEG, and 10 to 30 mM of a reducing agent for 12 to 18 hours at room temperature;
wherein the conjugation buffer solution comprises one or more of sodium acetate, phosphate acetate, potassium hydrogen phosphate, potassium dihydrogen phosphate, disodium hydrogen phosphate, potassium hydrogen phthalate, and sodium tetraborate, and has a pH in the range of 5.0 to 5.8; and
wherein the reducing agent comprises one or more of sodium cyanoborohydride, sodium triacetoxy borohydride, sodium borohydride, sodium dithionite, and sodium hydrosulfite.

3. The process of claim 2, wherein the conjugation buffer solution comprises sodium acetate;
wherein the reducing agent is 20 mM sodium cyanoborohydride;
wherein the conjugation reaction mixture is incubated for 12 to 16 hours;
wherein the PEG is 20kD PEG aldehyde; and
wherein the conjugation reaction mixture comprises 3 to 5 times more (w/w) 20kD PEG aldehyde than G-CSF.

4. The process of claim 2, further comprising:
viii. purifying the monopegylated G-CSF produced in step (vii) by cation exchange chromatography;
wherein the process yield of step (viii) ranges from 60% to 75%;
wherein the cation exchange chromatography comprises a stationary phase and a mobile phase;
wherein the stationary phase of the cation exchange chromatography in step (viii) is MacroCap-SP, SP Sepharose FF or Fractogel S03;
wherein the mobile phase in step (viii) comprises one or more of sodium acetate, acetic acid, and NaCl; and
wherein the mode of elution in step (viii) is step gradient, linear gradient, or a combination of both.

5. The process of claim 4, wherein the stationary phase of the cation exchange chromatography in step (viii) is MacroCap-SP;
wherein the mobile phase of the cation exchange chromatography in step (viii) comprises 10 to 50 mM sodium acetate; and
wherein the mode of elution in step (viii) is linear gradient.

6. The process of claim 4 further comprising, concentration of the purified monopegylated G-CSF by ultrafiltration to obtain a composition comprising 9-12 mg/ml monopegylated G-CSF.

7. The process of claim 6, wherein the ultrafiltration membrane has a cut-off value of 10 kDa.

8. The process of claim 1, further comprising washing the isolated inclusion bodies obtained from step (i) in one or more wash buffer for 60 to 90 minutes at a temperature in the range of 20 to 25° C.,
wherein the lysis buffer comprises 100 mM Tris, 250 mM EDTA, and 250 mM NaCl and has a pH in the range of 7.5 to 8.5;
wherein the isolating of inclusion bodies is performed with a combination of the laboratory scale sonicator and high pressure cell homogenizer;
wherein the wash buffer comprises one or more of Tris-EDTA-Triton buffer, Tris-EDTA-DOC buffer, Tris-NaCl-Urea buffer, Tris-buffer and TritonX-100;
wherein the wash buffer comprises one or more of 30 to 50 mM Tris, 3 to 7 mM EDTA, 0.1 to 0.5 M Urea, 1 to 2 M NaCl, and 0.8 to 1.5% Triton X 100; and
wherein the wash buffer has a pH in the range from 7.5 to 8.5.

9. The process of claim 1, wherein the solubilization buffer comprises 6 to 8 M urea, 20 to 50 mM Tris, and 2 to 7 mM EDTA;
wherein the pH of the solubilization reaction is maintained in the range of 9.5 to 10.5;
wherein the solubilization reaction comprises 20 to 100 mM cysteine; and
wherein the isolated inclusion bodies are incubated in the solubilization buffer for 2 to 3 hours.

10. The process of claim 1, further comprising clarifying the solubilized G-CSF obtained from step (ii) by centrifugation at 8000 to 15000 g.

11. The process of claim 1, wherein the refolding of the solubilized G-CSF comprises gradually diluting the solubilized G-CSF into 10 volumes of the refolding buffer;
wherein the oxidizing agent in the refolding buffer is cystine;
wherein the refolding buffer comprises 50 mM Tris, 0.5M Urea, 5% Sorbitol, and 0 to 5 mM cystine; and
wherein the acidifying of the refolded G-CSF solution comprises adding sodium acetate to a final concentration of 20 mM and adding hydrochloric acid.

12. The process of claim 11, wherein the refolding reaction is incubated for 12 to 18 hours at room temperature;
wherein the refolding buffer comprises 2 mM cystine; and
wherein the pH of the acidified refolded G-CSF solution is in the range of 3.5 to 4.5.

13. The process of claim 12, wherein the pH of the acidified refolded G-CSF solution is 4.0.

14. The process of claim 1, wherein the clarifying the acidified G-CSF solution in step (v) comprises microfiltration with a 0.2 μm filter;
wherein the stationary phase of the cation exchange chromatography in step (vi) is SP-Sepharose FF, CM-Sepharose FF, SP-Sepharose HP, Fractogel SO3 or Fractogel SE HiCap;
wherein the mobile phase of the cation exchange chromatography in step (vi) comprises one or more of sodium acetate, acetic acid, sodium phosphate, orthophosphoric acid, and sodium chloride;
wherein the stationary phase of the hydrophobic interaction chromatography in step (vi) is Phenyl Sepharose FF, Butyl Sepharose, Nuviac-Prime, HEA hypercel, PPA hypercel, Phenyl Sepharose HP, MEP hyper cell or Capto adhere; and
wherein the mobile phase of the hydrophobic interaction chromatography in step (vi) comprises one or both of sodium acetate and acetic acid.

15. The process of claim 14,
wherein the stationary phase of the cation exchange chromatography in step (vi) is CM Sepharose FF;
wherein the mobile phase of the cation exchange chromatography in step (vi) comprises 40 mM sodium acetate; and
wherein the stationary phase of hydrophobic the interaction chromatography in step (vi) is Phenyl Sepharose FF.

* * * * *